United States Patent [19]

Sabbaghian et al.

[11] Patent Number: 5,147,379
[45] Date of Patent: Sep. 15, 1992

[54] INSERTION INSTRUMENT FOR VENA CAVA FILTER

[75] Inventors: Mehdy Sabbaghian, Baton Rouge, La.; Tony Barfield, Beaumont, Tex.; Patrick Schiele, Schenectady, N.Y.; David W. Newton, Baton Rouge, La.; Gregory J. Lormand, Baton Rouge, La.; Glen J. Schwartzberg, Baton Rouge, La.

[73] Assignee: Louisiana State University and Agricultural and Mechanical College, Baton Rouge, La.

[21] Appl. No.: 617,672

[22] Filed: Nov. 26, 1990

[51] Int. Cl.[5] .............................................. A61B 17/00
[52] U.S. Cl. ...................... 606/206; 606/200; 606/108
[58] Field of Search ................ 606/108, 200, 206; 128/772, 899

[56] References Cited

U.S. PATENT DOCUMENTS

| | | | |
|---|---|---|---|
| 3,060,972 | 10/1962 | Sheldon | 128/772 |
| 3,952,747 | 4/1976 | Kimmell | 606/200 |
| 4,943,297 | 7/1990 | Saveliev et al. | 606/200 |

*Primary Examiner*—Michael H. Thaler
*Attorney, Agent, or Firm*—William David Kiesel; Robert C. Tucker

[57] ABSTRACT

An improved insertion instrument for a vena cava filter is provided and includes a filter retainer attached to the catheter for preventing accidental ejection of the filter and for enabling retraction of the filter into the carrier body at any time prior to complete ejection; a directional control mechanism attached to the plunger housing for allowing a user to guide the filter retainer through a vascular network; and a simplified plunger locking mechanism on the plunger for preventing premature ejection of the filter.

2 Claims, 5 Drawing Sheets

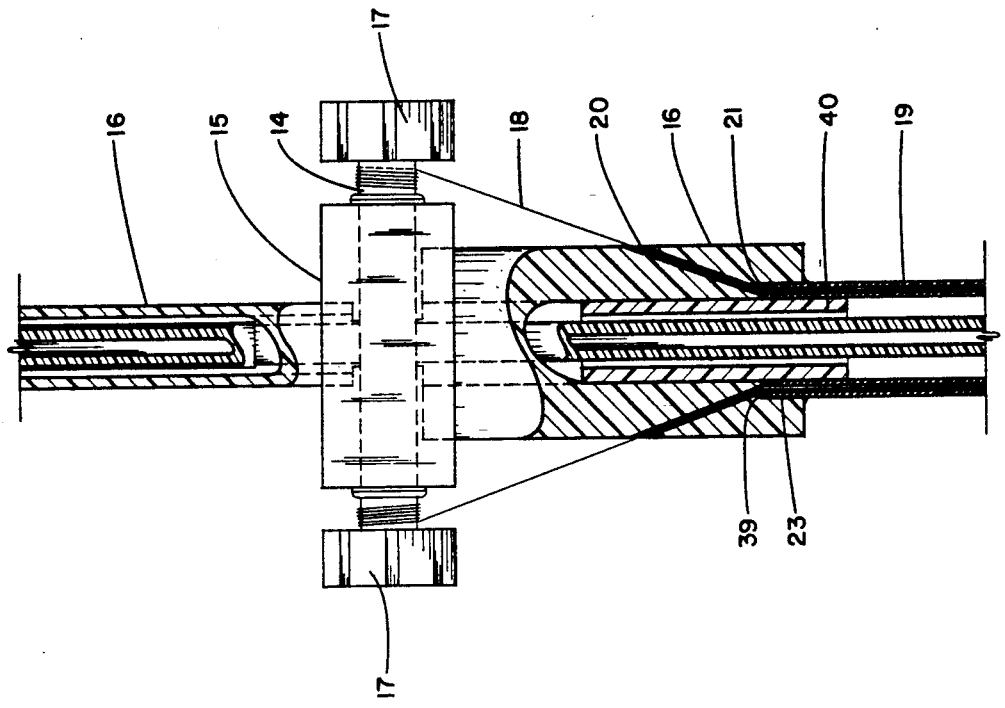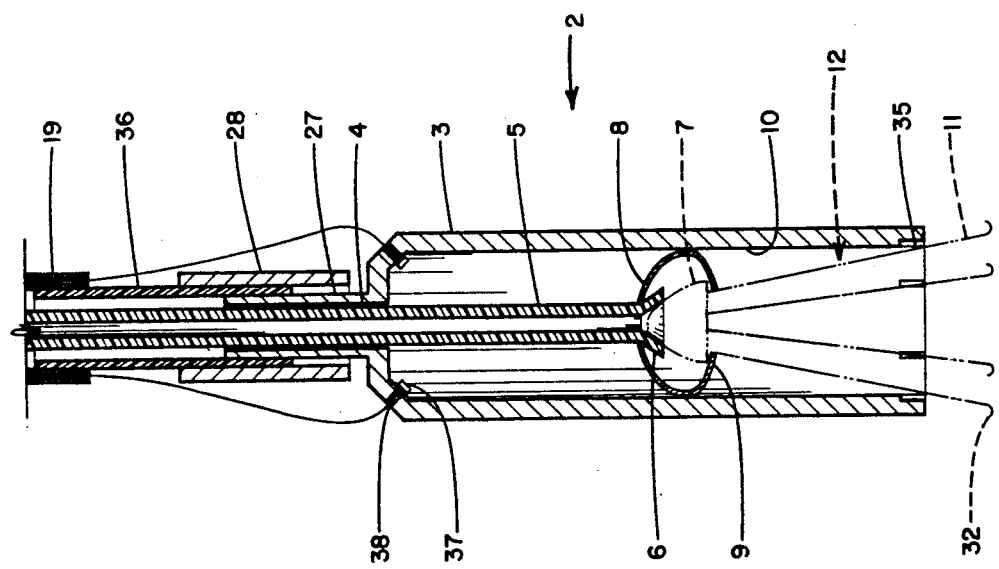

INSERTION INSTRUMENT FOR VENA CAVA FILTER

BACKGROUND OF THE INVENTION

1. Field of the Invention

This invention relates to instruments which are used particularly, though not exclusively, to place blood embolism filters in the circulatory system of humans or animals.

2. Prior Art

A common cause of death in hospitalized patients is the development of clots in the veins of the lower extremities, also known as deep vein thrombosis. Mortality associated with this condition is due to the occurrence of pulmonary emboli which travel from the lower extremities, through the chambers of the heart, and lodge in the pulmonary artery effectively obstructing blood flow to the lungs.

When a deep vein thrombosis occurs, the initial treatment relies on anti-coagulant therapy, which tends to prevent blood clot propagation as well as pulmonary emboli. However, such treatment is often contraindicated in about a third of all patients, especially in those who have undergone recent major operations due to the increased possibility of bleeding. In these cases, the focus of the treatment shifts to thrombus capture, rather than the prevention of thrombus propagation.

The most widely used method of thrombus capture is placement of a conically-shaped basket filter made of stainless steel into the inferior vena cava. The filter is introduced into the venous system in most instances by way of an incision in the internal jugular vein, and is placed in the appropriate position in the vessel under fluoroscopic control.

Before introduction into the body, the filter is placed with its legs restrained within a stainless steel retainer which is open at one end. The other end of the retainer is attached to a flexible plastic tube, which in turn is secured to a plunger device operated by the surgeon. The instrument is then inserted through the incision made at the jugular vein, and must be maneuvered through an intricate network of blood vessels to reach the lower vena cava destination. When the filter retainer is at the intended position, the filter is pushed out of the retainer by the plunger operated from outside the body. As the filter moves out of the retainer, the legs of the filter expand radially until the filter hooks penetrate the blood vessel wall and cause the filter to attach firmly within the vena cava.

The device currently used to implant blood embolism filters is commonly known as a jugular vein introducer catheter, which has been in use under the commercial name of Greenfield Vena Cava Filter System manufactured by Medi-tech, Inc., and which is described in U.S. Pat. No. 3,952,747 issued to Garman O. Kimmell on Apr. 27, 1976 and entitled "Filter and Filter Insertion Instrument". This device operates in the manner previously described, but has several deficiencies which the invention proposed herein attempts to overcome.

First, the only control that the surgeon has while maneuvering the catheter toward the lower vena cava is by way of the flexion in the plastic tubing connected to the filter retainer. The instrument must negotiate several sharp turns in its passage through the vessels and must do so without injury to the internal vessel walls. In addition, the surgeon must ensure that the instrument does not inadvertently enter any of the other branches leading away from the vena cava. In the current device, such problems may require the surgeon to completely remove the catheter, manually bend the plastic tube to make it conform to the path of the vessels, and reinsert it for a second trial at filter placement. This procedure is necessarily attended with a greater chance of injury to the recipient, as the risks to the patient grow exponentially as the required time for the operation increases. Furthermore, financial cost factors such as operating room time, surgical supplies, and anesthesia are increased significantly as additional time is spent readjusting the instrument during surgery.

Second, the design of the current device allows only for a pushing of the filter into the blood vessel, making it impossible for the surgeon to retract the filter back into the retainer should he decide to place it in a different location. As the filter is pushed by the plunger from the retainer, the position of the filter is irreversible such that the surgeon is helpless to correct the problem by way of the insertion instrument, and the filter may be misplaced or misaligned. Another disadvantage of the current device's inability to retract the filter is due to the inherent tendency of the filter to leave the retainer quickly and erratically during filter expansion as the strain energy in the legs of the stored filter is released. This uncontrollable ejection from the retainer can result in an implantation that is often less then optimum. Consequently, in either of these situations where the filter is improperly placed, the only recourse is to either accept the placement of the filter in its inefficient location, or to remove the filter by major surgery. Both of these alternatives are costly, time-consuming and often dangerous to the patient.

Yet another feature that is lacking in the current device is a means for keeping the filter legs and hooks from entangling each other when the filter is contained within the filter retainer. There is likewise no way of ensuring that the hooks impale the blood vessel equally spaced from one another. The danger of ejecting a filter whose legs are crossed is that the filter may not be implanted securely and may be out of line with the axis of the blood vessel. If this happens, the result could be migration of the filter in the direction of the heart, or in the least, inefficient trapping of emboli in the case of unequally spaced filter legs. The current device may include a filter loader designed to place the filter within the carrier, but there is no method for assuring that the filter legs will remain entangled and equally spaced during the filter's passage to the implantation site.

Finally, the existing art is equipped with a plunger locking device consisting of a threaded knob which tightens against the plunger. While this mechanism serves the purpose of preventing accidental ejection of the filter until the catheter is in the proper location, it is difficult to disengage it with one hand in the operating room environment. Twisting the knob with blood-covered surgical gloves is cumbersome, and does not provide a positive means of engagement or disengagement for the surgeon during the operation and distracts the surgeon's attention from the primary goal of proper filter placement.

Ideally, a filter insertion instrument used to implant blood embolism occlusion devices should not only provide the surgeon with a means for dependably retaining and retracting the filter during the operation, but should also enable the legs to remain equally spaced prior to and during implantation. Such a device should also allow for maximum control of the instrument in its passage through the complex vascular system as well as a locking device which is simple and reliable when used in a surgical environment.

SUMMARY OF THE PRESENT INVENTION

Therefore, it is an object of this invention to provide an improved insertion instrument capable of safely and reliably implanting an intra-vascular occlusion device into a blood vessel.

Another object of this invention is to provide a device which will facilitate the placement of a blood embolism filter by incorporating a directional control system to navigate the retainer through the vascular system.

A further object of this invention is to provide a device which incorporates a directional control system so that the filter retainer can be centered within the blood vessel, thereby allowing the filter to exit the retainer coaxially with the vessel and assuring optimum filter orientation.

An additional object of the device is to provide a means for relocating the filter by retracting the blood embolism filter within the retainer prior to releasing it into the blood vessel.

A further object of the device is to provide a means for preventing a blood embolism filter from prematurely ejecting itself from the filter retainer due to the release of stored energy in the legs of the filter.

Another object of the device is to provide a means for preventing entanglement of the filter legs prior to implantation and ensuring that the filter legs remain equally spaced during their impalement of the vessel wall.

Yet another object of the present invention is to provide an insertion instrument with a plunger lock method that is simpler, quicker and more reliable when used in a surgical environment.

Other objects, advantages and novel features of the present invention will become apparent to those skilled in the relevant art and to others from the following detailed description of the invention when considered in conjunction with the accompanying drawings.

Accordingly, an improved insertion instrument for implanting a blood embolism filter in a blood vessel is disclosed comprising at least one of the following components: (1) a filter retainer for carrying such a filter and having means allowing for retention and retraction of the filter prior to release, (2) a filter leg alignment means for ensuring equal spacing between the filter legs prior to impalement of the filter hooks into the blood vessel, (3) a directional control means for guiding the filter retainer through the vascular system, or (4) a simplified plunger locking means capable of preventing accidental movement of the plunger before the proper filter site is located.

BRIEF DESCRIPTION OF THE DRAWINGS

FIG. 2 is a sectional view of a preferred embodiment of the filter retainer showing the filter in a retained position within the carrier body as well as the relationship between the control wires and the filter retainer.

FIG. 3 is a sectional view of the upper portion of a preferred embodiment of the directional control means showing the relationship between the plunger housing and the flexible tube.

PREFERRED EMBODIMENT OF THE INVENTION

Figure 1:
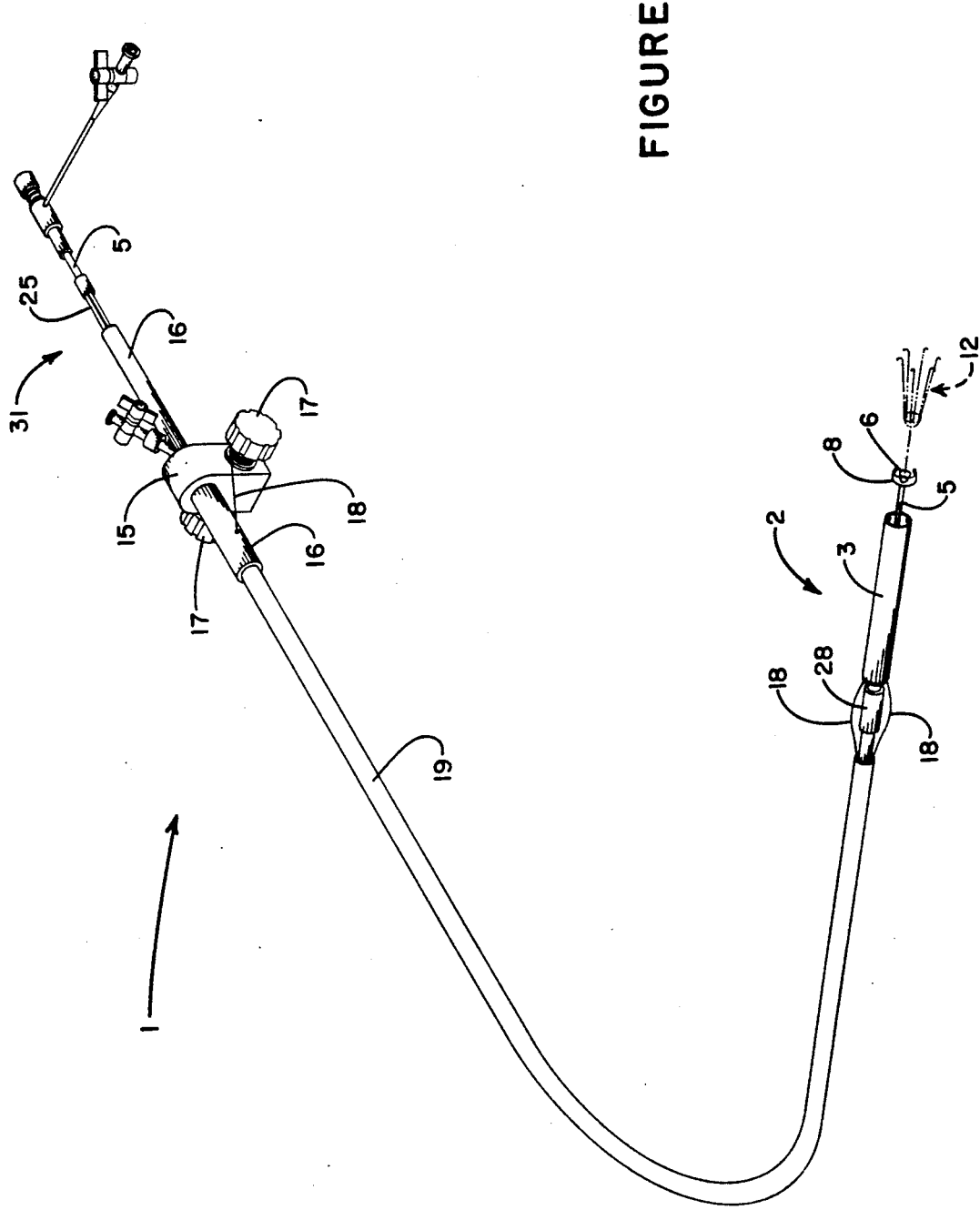
FIG. 1 is an overall view of a preferred embodiment of the improved insertion instrument for implanting a blood embolism filter in a blood vessel.

An improved insertion instrument for implanting a blood embolism filter 1 is depicted in an overall view in FIG. 1. In a preferred embodiment in FIG. 2, the instrument includes a filter retainer 2 having a cylindrical, hollow carrier body 3 with a plunger bore 4 whose axis is coaxial to the carrier body 3. Extending from the bottom of the carrier body 3 is an externally threaded carrier base 27 onto which is attached an internally threaded collar 28 which grips an annular sleeve 36 attached to the flexible tube 19. The plunger 5 is capable of reciprocating through the carrier body 3 and the carrier base 27 and includes a plunger tip 6 which makes contact with the filter hub 7 once the instrument is loaded with the filter 12. Attached near the end of the plunger tip 6 is a filter retaining clamp 8 whose clamp arms 9 are resiliently compressed by the inner surface 10 of the carrier body 3 to the extent that the filter hub 7 is urged forcibly against the plunger tip 6.

The carrier body 3 has several filter leg alignment slots 35 depicted in FIG. 2 formed into inner surface and extending parallel to the axis of the carrier body 3. The alignment slots 35 are equal in number to the number of filter legs 11 and are equally spaced about the inside of the carrier body 3. As the filter 12 is carried within the carrier body 3, the filter hooks 32 are kept within the alignment slots 35, thus preventing entanglement of the filter legs 11 and ensuring equal spacing between them.

Figure 5:
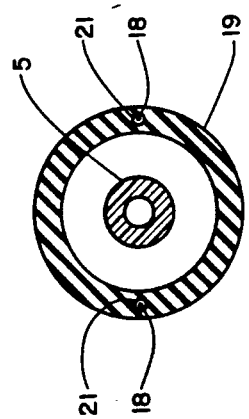
FIG. 5 is a cross-sectional view of the flexible tube showing the relationship between the main bore and the control wire bores.

In a preferred embodiment, the directional control means 13 partially depicted in FIG. 3 includes a rotatable control shaft 14 in communication with a shaft housing 15 which is in turn secured to the plunger housing 16. The control shaft 14 is rotated by way of control knobs 17, and each of two control wires 18 is wound about opposite sides of the control shaft 14 in opposing directions so as to allow slack in one as tension is applied to the other. The control wires 18 communicate with the flexible tube 19 by way of wire bores 20 formed through the plunger housing 16, where they each enter a control wire bore 21 formed on each side of, and extending along the length of, the flexible tube 19. A cross-section of this tube is shown in FIG. 5. The control wires 18 slide within the control wire bores 21 and, in a preferred embodiment shown in FIG. 2, exit the flexible tube 19 near the filter retainer 2 and are attached at the bottom of the carrier body 3 at 180 degrees apart in any manner that will ensure a reliable connection between the carrier body 3 and the control shaft 14. FIG. 2 shows an attachment method consisting of a wire stop 37 fixed to each control wire 18 capable of preventing passage through control bores 38 formed into the carrier body 3. While the control wires 18 may be attached virtually anywhere along the length of the filter retainer 2, including the collar 28, an attachment similar to the preferred embodiment will provide the largest feasible moment arm and the best range of movement of the filter retainer 2. As shown in FIG. 3, the upper portion of the flexible tube 19 communicates with an annular rim 39 formed in the plunger housing 16 by a seal 22 that securely bonds the flexible tube 19 between the inner bore 23 of the plunger housing 16 and a plunger housing sleeve 40 also bonded to the plunger housing 16.

Figure 6:
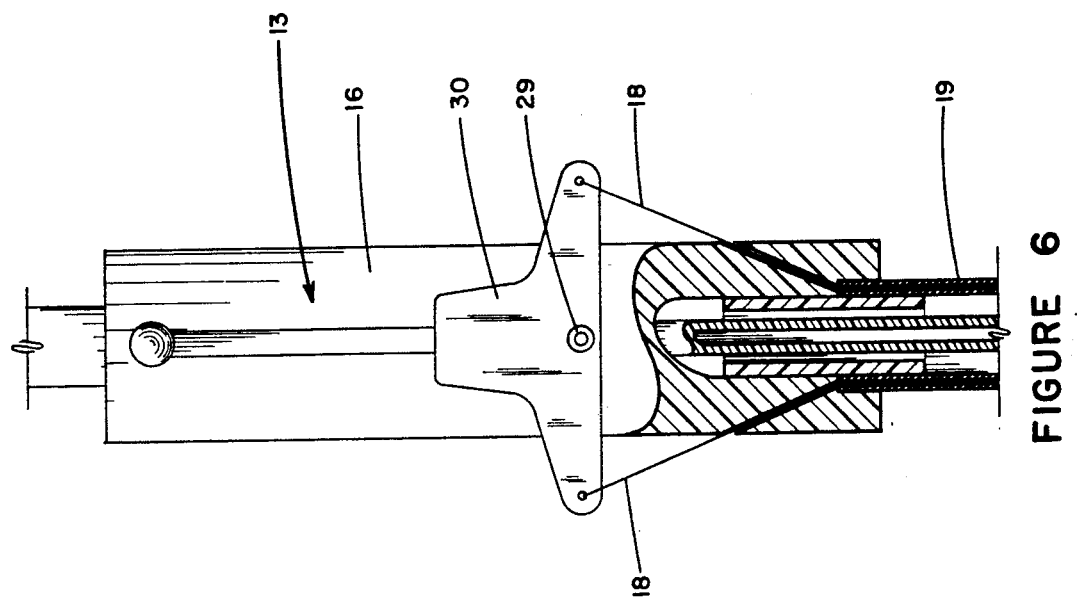
FIG. 6 is a front view of an alternate embodiment of the directional control means depicting the relationship between the control handle, the control wires, and the plunger housing.

In an alternate embodiment of the upper portion of the directional control means 13 partially depicted in FIG. 6, a pivot 29 is secured to the plunger housing 16 to which a control handle 30 is pivotally attached. Each of two control wires 18 is attached to the control handle 30 on either side of the pivot 29. In this embodiment, the control handle 30 is simply moved to either side to apply tension to one control wire 18 while allowing slack on the other.

Figure 4:
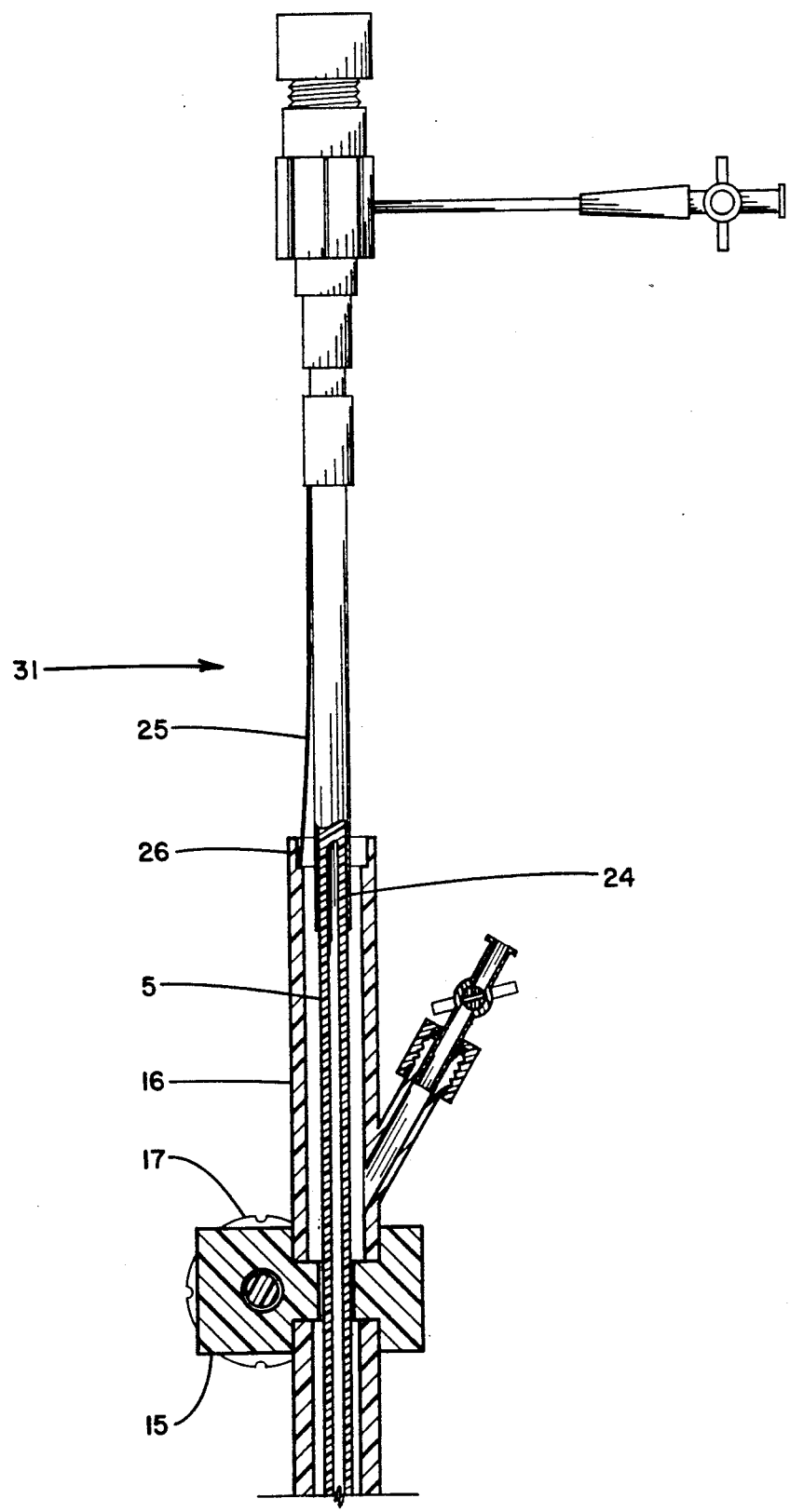
FIG. 4 is a view of the preferred embodiment of the plunger locking means showing the plunger in a locked position.
Figure 7:
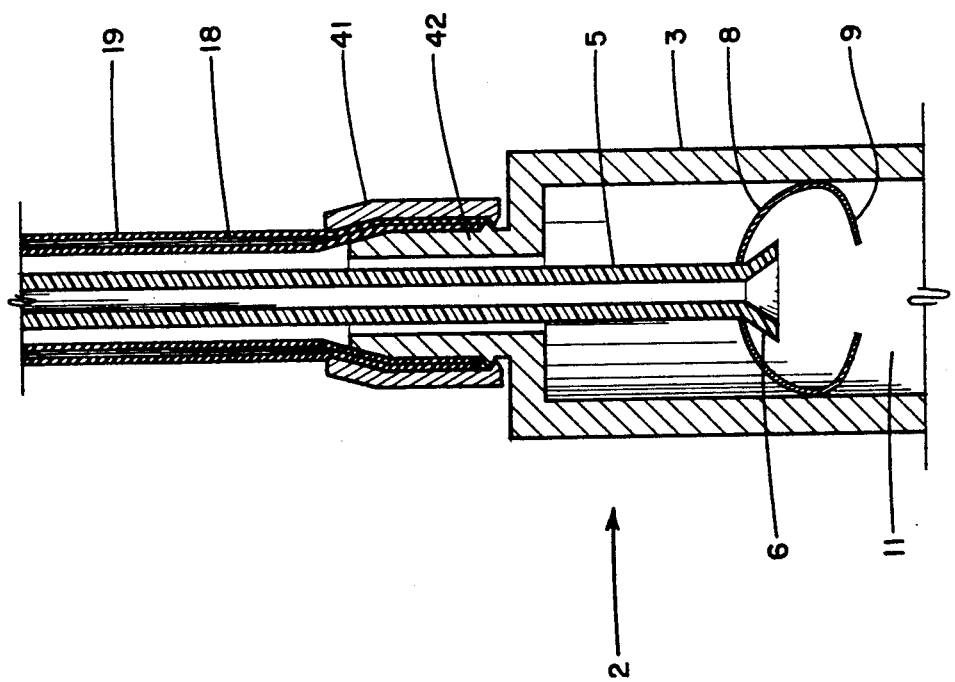
FIG. 7 is a sectional view of an alternate embodiment of the lower directional control means showing a proposed method of attachment of the flexible tube to the filter retainer.

In an alternate embodiment of the lower directional control means 13 partially depicted in FIG. 7, the flexible tube 19 and the control wires 18 are pressed securely between a snap collar 41 and a non-threaded carrier base 42 forming a seal. This arrangement, however, provides less of a moment arm for directional control and the strength of the attachment of the control wires 18 at this point is not optimum. In a preferred embodiment of the plunger locking means 31, a rigid sleeve 24 is attached to the plunger 5 above the plunger housing 16 as shown in FIG. 4. An elongated leaf spring 25 is secured to the rigid sleeve 24 and communicates in a locked position with an internal axial flange 26 that is formed at the top of the plunge housing 16.

Figure 8:
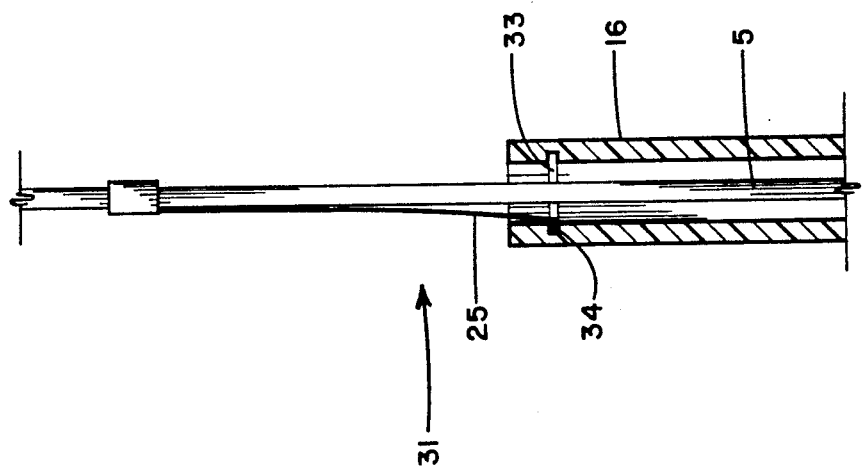
FIG. 8 is a sectional view of an alternate embodiment of the plunger locking means depicting the relationship between the leaf spring and the plunger housing.

In an alternate embodiment of the plunger locking means 31 depicted in FIG. 8, an internal annular channel 33 is formed in the plunger housing 16. The leaf spring 25 includes an outwardly bent lock section 34 which communicates with the annular channel 33 and prevents motion of the plunger 5 in either direction.

In operation, an incision is made in the jugular vein to allow for entry of the instrument 1. To load the filter 12 into the device, the filter retaining clamp 8 is pushed out of the carrier body 3 by the plunger 5 to open the clamp arms 9. The filter hub 7 is placed within the clamp arms 9, and the plunger 5 is pulled back to stow the filter 12 inside the carrier body 3. Once the filter 12 is completely contained, the filter hooks 32 should be placed within the alignment slots 35 provided on the inner surface of the carrier body 3 to prevent entanglement of the filter legs 11 and maintain their equal spacing.

The filter retainer 2 is placed in the incision and is guided through the vascular network by operation of the directional control means 13. As the filter retainer 2 reaches a cross-roads in the vessel, the control knob 17 is turned to apply tension to one of the control wires 18 which pulls the filter retainer 2 in the desired direction. When the point of implantation is reached, the plunger locking means 31 is released by depressing the leaf spring 25 away from the axial flange 26 and toward the rigid sleeve 24 of the plunger 5. The plunger 5 is thereafter urged through the flexible tube 19 and the carrier body 3.

Should it become necessary at this point to relocate the filter retainer 2 for placement of the filter 12 in a different position, the plunger 5 may be retracted causing the filter 12 to return within the carrier body 3. When the plunger returns to its original position, the leaf spring 25 resiliently expands back against the axial flange 26 on the plunger housing 16, thus preventing downward motion of the plunger 5 until the leaf spring 25 is depressed again.

Upon final and complete actuation of the plunger 5, the filter legs 11 expand radially as the filter 12 is pushed from the carrier body 3. The filter leg alignment slots 35 ensure that the filter legs 11 expand at equal spacing with respect to each other and assist in centering the filter 12 in a co-axial position with the blood vessel as the filter hooks 32 begin to impale themselves. As the clamp arms 9 clear the inner surface 10 of the carrier body 10, they expand outwardly, thereby releasing their grip on the filter hub 7 and allowing the filter 12 to function in its occlusive capacity.

Many other variations, modifications, and alternate embodiments may be made in the apparatus and techniques hereinbefore described, by those having experience in this technology, without departing from the concept of the present invention. Accordingly, it should be clearly understood that the apparatus and methods depicted in the accompanying drawings and referred to in the foregoing description are illustrative only and are not intended as limitations on the scope of this invention, as defined in the following claims.

What we claim is:

1. In an insertion instrument for positioning a filter in a blood vessel, including a carrier for carrying said filter to an implantation site in said blood vessel, an ejector actuating means and plunger means operatively connected to said carrier for ejecting the filter from said carrier, an elongated flexible tube connected at one end to said carrier for advancing said carrier to the intended filter placement location, and a plunger housing secured to said flexible tubing at an end opposite said carrier to provide a guide for said ejector actuating means and a rigid structure for securing other associated component parts, the improvement of which comprises means operatively connected to said plunger means within said carrier for retaining and retracting said filter prior to release of said filter into the blood vessel, wherein said means for retaining and retracting comprises:

(i) a plunger tip at the end of said plunger means for making contact with said filter and ejecting said filter from said carrier;

(ii) a resilient clamping means secured to said plunger means compressed while within said carrier for retaining said filter prior to complete ejection, resiliently expanding upon exiting said carrier and thereby releasing said filter into said blood vessel; and (iii) a plurality of filter leg alignment slots formed into the inner surface of said carrier for maintaining equal spacing between said filter legs and guiding said filter legs as said filter is ejected into said blood vessel.

2. In an insertion instrument for positioning a filter in a blood vessel, including a carrier for carrying said filter to an implantation site in said blood vessel, an ejector actuating means and plunger means operatively connected to said carrier for ejecting the filter from said carrier, an elongated flexible tube connected at one end to said carrier for advancing said carrier to the intended filter placement location, and a plunger housing secured to said flexible tubing at an end opposite said carrier to provide a guide for said ejector actuating means and a rigid structure for securing other associated component parts, the improvement of which comprises:

(i) a simplified plunger locking means secured to said ejector actuating means for preventing said plunger means from movement through said plunger housing prior to filter ejection, said plunger locking means comprising:

(a) a rigid sleeve axially secured to said plunger means opposite said filter retainer and above said plunger housing;

(b) an internal axial flange in the upper end of and concentric with said plunger housing; and (c) an elongated resilient member secured on one end to said rigid sleeve above said internal axial flange and restrained on the other end by resilient expansion against said internal axial flange to prevent movement of said plunger means prior to filter ejection.

* * * * *